United States Patent
Lee et al.

(10) Patent No.: US 10,185,883 B2
(45) Date of Patent: Jan. 22, 2019

(54) MOBILE TERMINAL AND METHOD FOR CONTROLLING SAME

(71) Applicant: LG ELECTRONICS INC., Seoul (KR)

(72) Inventors: Junhak Lee, Seoul (KR); Yonghan Lee, Seoul (KR); Byeongkil Ahn, Seoul (KR); Donghyeon Kim, Seoul (KR); Hyungchul Won, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 45 days.

(21) Appl. No.: 15/322,083

(22) PCT Filed: Jan. 9, 2015

(86) PCT No.: PCT/KR2015/000212
§ 371 (c)(1),
(2) Date: Dec. 23, 2016

(87) PCT Pub. No.: WO2015/199304
PCT Pub. Date: Dec. 30, 2015

(65) Prior Publication Data
US 2017/0161577 A1 Jun. 8, 2017

(30) Foreign Application Priority Data

Jun. 27, 2014 (KR) .................. 10-2014-0079475

(51) Int. Cl.
*G06K 7/00* (2006.01)
*G06K 9/00* (2006.01)
(Continued)

(52) U.S. Cl.
CPC ........ *G06K 9/00892* (2013.01); *A61B 5/0261* (2013.01); *A61B 5/1032* (2013.01);
(Continued)

(58) Field of Classification Search
USPC .................... 382/116, 312; 340/5.2
See application file for complete search history.

(56) References Cited

U.S. PATENT DOCUMENTS 5,088,817 A * 2/1992 Igaki .................. G06K 9/00046
250/556
8,917,158 B2 * 12/2014 Bong ...................... G06F 3/016
340/5.53

(Continued)

FOREIGN PATENT DOCUMENTS

JP 2008244698 10/2008
JP 2013232197 11/2013
(Continued)

OTHER PUBLICATIONS

PCT International Application No. PCT/KR2015/000212, Written Opinion of the International Searching Authority dated Mar. 27, 2015, 19 pages.

*Primary Examiner* — Kathleen Y Dulaney
(74) *Attorney, Agent, or Firm* — Lee, Hong, Degerman, Kang & Waimey

(57) ABSTRACT

The present invention relates to a mobile terminal capable of a new type of user input, comprising: a backside input unit including a plurality of buttons and exposed to the backside of the mobile terminal; a memory for storing relationships between combinations of the plurality of buttons and control instructions of the mobile terminal and biometric information; a sensor unit, arranged on the backside of the mobile terminal and adjacent to the backside input unit, for sensing a user's bio signal; and a control unit for, upon receiving a user input in accordance with a particular combination of the plurality of buttons, controlling the sensor unit to sense the user's bio signal, and authenticating the user using the sensed bio signal and the stored biometric information.

10 Claims, 9 Drawing Sheets

(51) Int. Cl.
  *G05B 19/00* (2006.01)
  *G06F 21/32* (2013.01)
  *H04B 1/40* (2015.01)
  *A61B 5/026* (2006.01)
  *A61B 5/103* (2006.01)
  *A61B 5/1172* (2016.01)
  *A61B 5/00* (2006.01)

(52) U.S. Cl.
  CPC ............ *A61B 5/1172* (2013.01); *A61B 5/489* (2013.01); *A61B 5/6897* (2013.01); *G06F 21/32* (2013.01); *G06K 9/0004* (2013.01); *G06K 9/00087* (2013.01); *G06K 9/00899* (2013.01); *H04B 1/40* (2013.01); *G06K 2009/00932* (2013.01); *G06K 2009/00939* (2013.01)

(56) References Cited

U.S. PATENT DOCUMENTS

| | | | | |
|---|---|---|---|---|
| 2005/0063567 | A1* | 3/2005 | Saitoh | G06K 9/00013 382/115 |
| 2008/0095412 | A1* | 4/2008 | Fujieda | A61B 5/02007 382/124 |
| 2010/0240415 | A1* | 9/2010 | Kim | G06F 3/03547 455/565 |
| 2011/0050393 | A1* | 3/2011 | Kang | G06F 21/32 340/5.53 |
| 2011/0129128 | A1* | 6/2011 | Makimoto | G06K 9/00013 382/124 |
| 2011/0254780 | A1* | 10/2011 | Kim | G06F 1/1626 345/173 |
| 2013/0015946 | A1* | 1/2013 | Lau | G07C 9/00 340/5.2 |
| 2014/0004907 | A1* | 1/2014 | Kim | H04M 1/72519 455/566 |
| 2014/0184824 | A1* | 7/2014 | Matsuda | H04N 7/183 348/207.1 |
| 2014/0212008 | A1* | 7/2014 | Hatcher, II | G06K 9/00033 382/124 |
| 2014/0225821 | A1* | 8/2014 | Kim | H04M 1/236 345/156 |
| 2014/0347330 | A1* | 11/2014 | Kim | G06F 1/1637 345/184 |
| 2014/0369572 | A1* | 12/2014 | Setlak | G06K 9/00013 382/124 |
| 2015/0003693 | A1* | 1/2015 | Baca | G06F 21/00 382/124 |
| 2015/0078633 | A1* | 3/2015 | Hung | G06K 9/00114 382/124 |
| 2015/0098631 | A1* | 4/2015 | Palmer | G06K 9/00288 382/118 |
| 2015/0237192 | A1* | 8/2015 | Kim | H04W 4/90 455/404.1 |
| 2015/0269409 | A1* | 9/2015 | Weber | G06F 3/044 382/125 |
| 2016/0034738 | A1* | 2/2016 | Luo | G06K 9/001 382/125 |
| 2016/0173673 | A1* | 6/2016 | Hyun | H04M 1/236 455/566 |

FOREIGN PATENT DOCUMENTS

| | | |
|---|---|---|
| KR | 1020100084148 | 7/2010 |
| KR | 1020120122587 | 11/2012 |
| KR | 101397089 | 5/2014 |

* cited by examiner

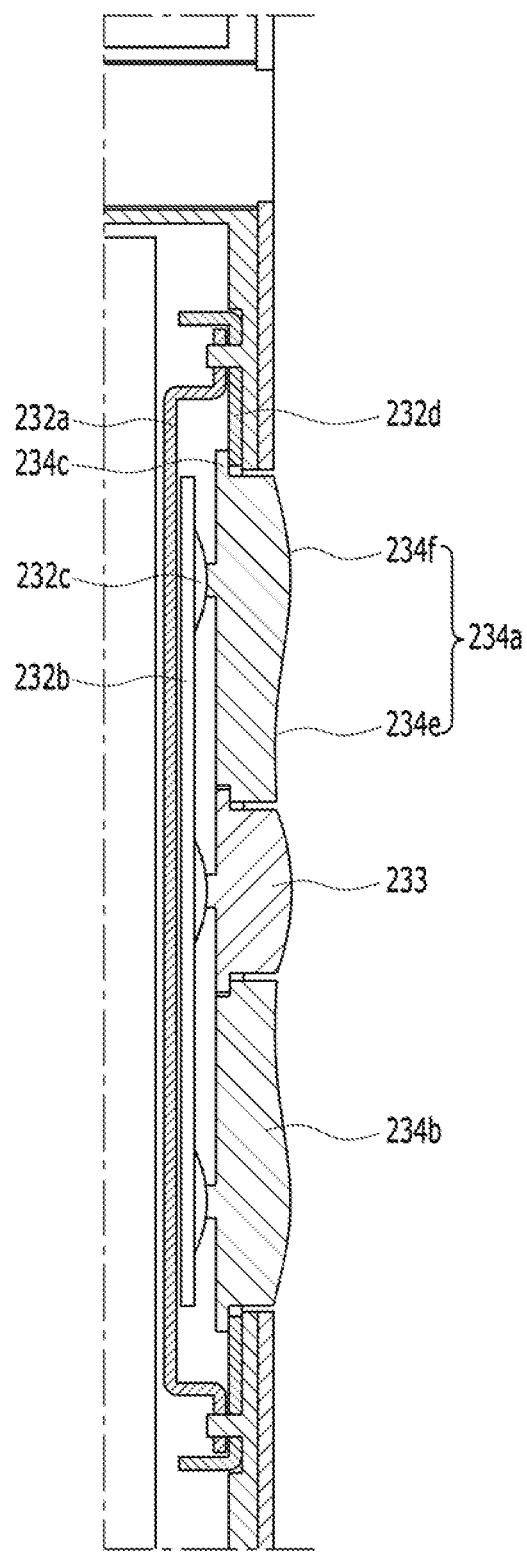

MOBILE TERMINAL AND METHOD FOR CONTROLLING SAME

CROSS-REFERENCE TO RELATED APPLICATIONS

This application is the National Stage filing under 35 U.S.C. 371 of International Application No. PCT/KR2015/000212, filed on Jan. 9, 2015, which claims the benefit of earlier filing date and right of priority to Korean Application No. 10-2014-0079475, filed on Jun. 27, 2014, the contents of which are all hereby incorporated by reference herein in their entirety.

TECHNICAL FIELD

The present invention relates to a mobile terminal having an input unit and a biometric authentication sensor at a rear side thereof and method for controlling the same.

BACKGROUND ART

Terminals may be generally classified as mobile/portable terminals or stationary terminals according to their mobility. Mobile terminals may also be classified as handheld terminals or vehicle mounted terminals according to whether or not a user can directly carry the terminal.

As functions of the terminal are getting diversified, the terminal tends to be implemented as a multimedia player with multiple functions of capturing images or videos, playing back music files or video files, gaming, and receiving broadcasting programs, and the like.

Various attempts have been made to implement complicated functions of such a multimedia player by means of hardware or software. For example, a user interface environment is provided to allow users to easily and conveniently search for and select functions.

Also, as a mobile terminal is considered as a personal belonging for expressing his or her own personality, various design forms are requested. The design forms include structural modifications and improvements in order for a user to more easily use the mobile terminal. As one of structural alterations and improvements, a manipulation unit may be considered.

However, the manipulation unit provided separately from a touch screen hinder slim and simple designs of the terminal. In addition, there may be a problem such as reducing a display area due to the manipulation unit disposed at a lateral surface of the mobile terminal. Accordingly, in order to solve such a problem, a manipulation unit with a new structure and an input method thereof may be taken into consideration.

Further, a method for authenticating a user more accurately and securely is also required.

DISCLOSURE OF THE INVENTION

Technical Task

One technical task of the present invention is to provide a mobile terminal capable of receiving a new type of user input different from the conventional one.

Another technical task of the present invention is to provide a mobile terminal capable of improving accuracy in user authentication.

Technical Solutions

In one technical aspect of the present invention, provided is a mobile terminal, including: a rear input unit including a plurality of buttons, which is exposed at a rear side of the mobile terminal; a memory for storing relationships between combinations of the plurality of the buttons and control commands of the mobile terminal and biometric information; a sensor unit for sensing a biometric signal of a user, which is disposed adjacent to the rear input unit at the rear side of the mobile terminal; and a controller, wherein when a user input corresponding to a specific combination of the plurality of the buttons is received, the controller controls the sensor unit to sense the biometric signal of the user and authenticates the user by using the sensed biometric signal and the stored biometric information.

In this case, the rear input unit may be configured to include a fingerprint sensor for detecting a fingerprint of the user. In addition, the rear input unit may be configured to include a first button part and a second button part with buttons disposed on both top and bottom portions of the first button part.

The sensor unit may be disposed at the rear side of the mobile terminal such that the sensor unit is adjacent to a bottom portion of the rear input unit. In addition, the sensor unit may be configured to include a light source for emitting light to a finger of the user and an image sensor for sensing the biometric signal from reflected light reflected from the finger.

The biometric signal may indicate at least one of a pattern of a user's finger vein, a change in blood flow in a user's finger vein, and a change in color of a user's finger.

The controller may compare a pattern of a user's finger vein indicated by the sensed biometric signal with a vein pattern indicated by the stored biometric information and then authenticate the user in accordance with the comparison result. In addition, the controller may determine whether the biometric signal is forged or copied by using at least one of a change in blood flow in a user's finger vein and a change in color of a user's finger, which are indicated by the biometric signal.

In another technical aspect of the present invention, provided is a method of controlling a mobile terminal, including: receiving a user input corresponding to a combination of the plurality of the buttons included in a rear input unit disposed at a rear side of the mobile terminal, sensing a biometric signal of a user by using a sensor unit adjacent to the rear input unit in response to the user input; and authenticating the user by using the sensed biometric signal and pre-stored biometric information.

The method of controlling the mobile terminal with the rear input unit, which includes the plurality of the buttons and which is disposed at the rear side of the mobile terminal, may include the following.

The sensing of the biometric signal of the user may include emitting light to a finger of the user and sensing the biometric signal from reflected light reflected from the finger. In addition, the biometric signal of the user may be sensed by using the sensor unit disposed adjacent to a bottom portion of the rear input unit.

The authenticating the user may include comparing a pattern of a user's finger vein indicated by the sensed biometric signal with a vein pattern indicated by the pre-stored biometric information and authenticating the user in accordance with the comparison result.

Further, the controlling method of the present invention may further include determining whether the biometric signal is forged or copied by using at least one of a change in blood flow in a user's finger vein and a change in color of a user's finger, which are indicated by the biometric signal.

Advantageous Effects

According to the present invention, a user input unit can be disposed on a rear surface of a terminal, whereby a front display can be configured to have a larger screen. Moreover, by doing so, it is possible to achieve a new design such that a lateral surface of the terminal is configured to be inclined or have multiple layers. Furthermore, a new type of user interface can be implemented.

In addition, according to the present invention, it is possible to improve accuracy in user authentication by using a fingerprint or a biometric signal of a user.

DESCRIPTION OF DRAWINGS

FIGS. 4a and 4b are a detailed exploded view and a cross-sectional view of a rear input unit shown in FIG. 3.

BEST MODE FOR INVENTION

Figure 1:
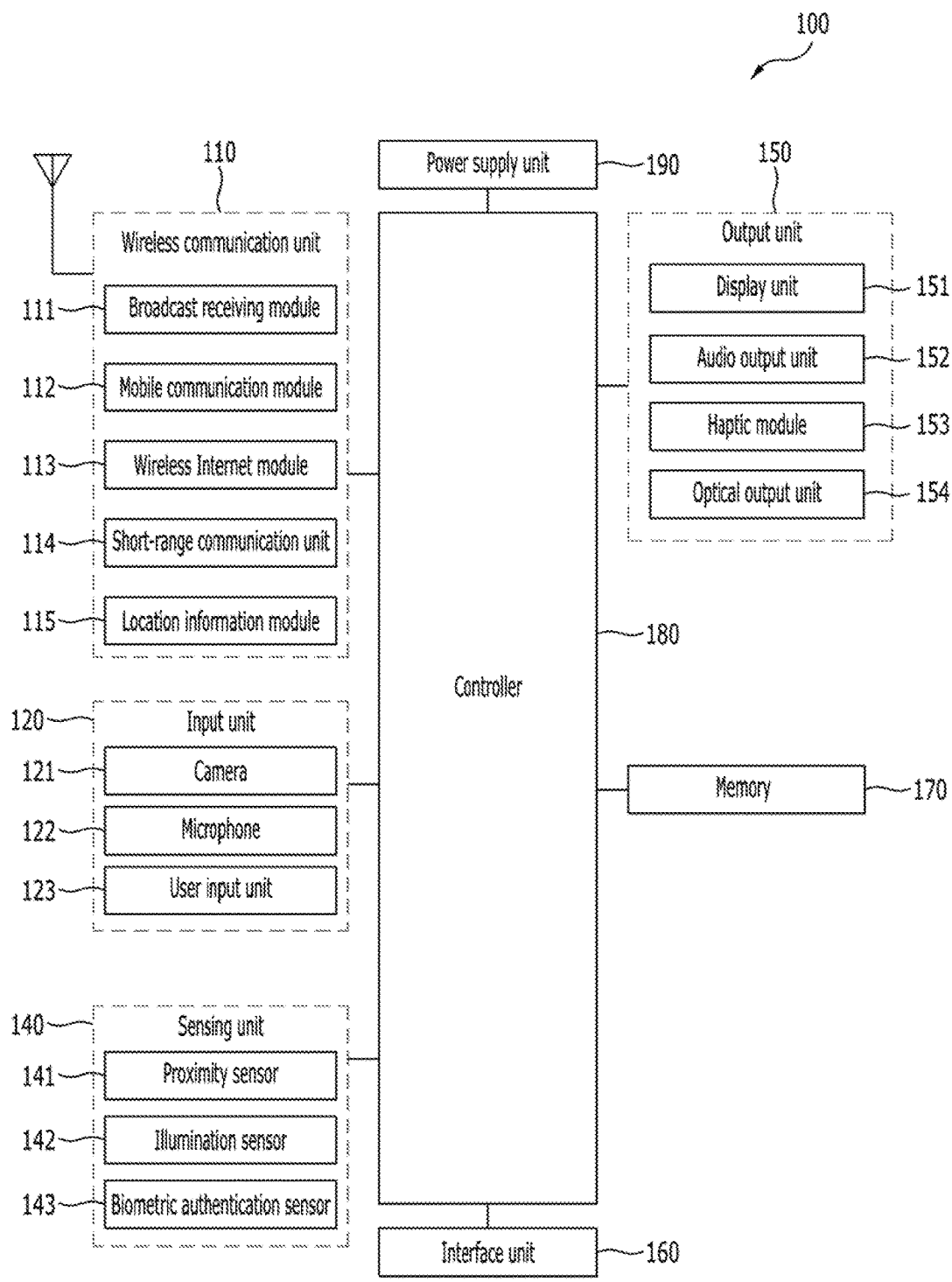
FIG. 1 is a block diagram of a mobile terminal according to one embodiment of the present invention.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a term such as "module" and "unit" may be used to refer to elements or components. Use of such a term herein is merely intended to facilitate description of the specification, and the term itself is not intended to give any special meaning or function. In the present invention, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present invention should be construed to extend to any alterations, equivalents and substitutes in addition to those which are particularly set out in the accompanying drawings.

It will be understood that although the terms first ($1^{st}$), second ($2^{nd}$), etc. may be used herein to describe various elements, and these elements should not be limited by these terms. These terms are generally only used to distinguish one element from another.

It will be understood that when an element is referred to as being "connected with" or "accessed by" another element, the element can be directly connected with or accessed by the other element or intervening elements may also be present. In contrast, when an element is referred to as being "directly connected with" or "directly accessed by" another element, there are no intervening elements present.

A singular representation may include a plural representation unless it represents a definitely different meaning from the context.

Terms such as "comprise", "include" or "have" are used herein and should be understood that they are intended to indicate an existence of several components, functions or steps, disclosed in the specification, and it is also understood that greater or fewer components, functions, or steps may likewise be utilized. Moreover, due to the same reasons, it is also understood that the present application includes a combination of features, numerals, steps, operations, components, parts and the like partially omitted from the related or involved features, numerals, steps, operations, components and parts described using the aforementioned terms unless deviating from the intentions of the disclosed original invention.

Mobile terminals presented herein may be implemented using a variety of different types of terminals. Examples of such terminals may include cellular phones, smart phones, laptop computers, digital broadcast terminals, personal digital assistants (PDAs), portable multimedia players (PMPs), navigators, slate PCs, tablet PCs, ultrabooks, wearable devices (for example, smart watches, smart glasses, head mounted displays (HMDs)), and the like.

By way of non-limiting example only, further description will be made with reference to particular types of mobile terminals. However, such teachings apply equally to other types of stationary terminals such as digital TVs, desktop computers, digital signage players and the like.

FIG. 1 is a block diagram of a mobile terminal according to one embodiment of the present invention.

A mobile terminal 100 may include components such as a wireless communication unit 110, an input unit 120, a sensing unit 140, an output unit 150, an interface unit 160, a memory 170, a controller 180, a power supply unit 190 and the like. It is appreciated that implementing all of the components shown in FIG. 1 is not a requirement, and that greater or fewer components may alternatively be implemented.

In particular, among the above-listed components, the wireless communication unit 110 typically includes one or more modules which permit communications such as wireless communications between the mobile terminal 100 and a wireless communication system, communications between the mobile terminal 100 and another mobile terminal 100, communications between the mobile terminal 100 and an external server. Further, the wireless communication unit 110 typically includes one or more modules which connect the mobile terminal 100 to one or more networks.

The wireless communication unit 110 may include at least one of a broadcast receiving module 110, a mobile communication module 112, a wireless Internet module 113, a short-range communication module 114, and a location information module 115.

The input unit 120 may include a camera 121 for an image or video signal input, a microphone 122 (or an audio input unit) for an audio signal input, and a user input unit 123 (e.g., a touch key, a push key (or mechanical key), etc.) for receiving an input of information from a user. Audio or image data collected by the input unit 20 may be analyzed and processed into user's control command.

The sensing unit 140 is typically implemented using one or more sensors configured to sense internal information of the mobile terminal 100, information on the surrounding environment of the mobile terminal 100, user information, and the like. For example, the sensing unit 140 may include a proximity sensor 141 and an illumination sensor 142. If desired, the sensing unit 14 may alternatively or additionally include other types of sensors or devices, such as a touch sensor, an acceleration sensor, a magnetic sensor, a gravity sensor (G-sensor), a gyroscope sensor, a motion sensor, an RGB sensor, an infrared (IR) sensor, a finger scan sensor, a ultrasonic sensor, an optical sensor (for example, the camera 121), the microphone 122, a battery gauge, an environment sensor (for example, a barometer, a hygrometer, a thermometer, a radiation detection sensor, a thermal sensor, and a gas sensor, etc.), and a chemical sensor (for example, an electronic nose, a health care sensor, a biometric authentication sensor, etc.), to name a few. The mobile terminal 100 disclosed in the present specification may be configured to utilize information obtained from at least two of the above-listed sensors.

The output unit 150 is typically configured to output various types of information, such as audio, video, tactile output, and the like. The output unit 150 may include at least one of a display unit 151, an audio output unit 152, a haptic module 153, and an optical output unit 154. The display unit 151 may have an inter-layered structure or an integrated structure with a touch sensor in order to facilitate a touch-screen. The touchscreen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include at least one of wired or wireless headset ports, external power supply ports, wired or wireless data ports, memory card ports, ports for connecting a device having an identification module, audio input/output (I/O) ports, video I/O ports, earphone ports, and the like. In some cases, the mobile terminal 100 may perform appropriate control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or commands for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operations of the mobile terminal 100, in addition to the operations associated with the application programs. The controller 180 may provide or process information or functions appropriate for a user by processing signals, data, information and the like, which are inputted or outputted by the various components depicted in the above description, or running application programs stored in the memory 170.

Moreover, in order to launch an application program stored in the memory 170, the controller 180 can control at least one portion of the components described with reference to FIG. 1. Furthermore, the controller 180 controls at least two of the components included in the mobile terminal 100 to be activated in combination to launch the application program.

The power supply unit 190 can be configured to receive external power or provide internal power in order to supply appropriate power required for operating elements and components included in the mobile terminal 100. The power supply unit 190 may include a battery. In particular, the battery may include be a built-in battery or a replaceable (or detachable) battery.

At least some of the components can operate cooperatively to implement the operations, controls or controlling methods of the mobile terminal 100 according to various embodiments mentioned in the following description. In addition, the operation, control or controlling method of the mobile terminal 100 may be implemented on the mobile terminal 100 by launching at least one application program stored in the memory 170.

Before describing the various embodiments related to the above-mentioned mobile terminal 100, the components depicted in this figure will now be described in more detail with reference to FIG. 1.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some cases, two or more broadcast receiving modules 111 may be utilized to facilitate simultaneously receiving of two or more broadcast channels, or to support switching among broadcast channels.

The mobile communication module 112 can transceive radio signals with one or more network entities. Typical examples of a network entity include a base station, an external mobile terminal, a server, and the like. Such network entities form part of a mobile communication network, which is constructed according to technical standards or communication methods for mobile communications (for example, GSM (Global System for Mobile communication), CDMA (Code Division Multi Access), CDMA2000 (Code Division Multi Access 2000), EV-DO (Enhanced Voice-Data Optimized or Enhanced Voice-Data Only), WCDMA (Wideband CDMA), HSDPA (High Speed Downlink Packet Access), HSUPA (High Speed Uplink Packet Access), LTE (Long Term Evolution), LTE-A (Long Term Evolution-Advanced), and the like).

The above-described radio signals may include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive radio signals via communication networks according to wireless Internet technologies.

Examples of such a wireless Internet technology include WLAN (Wireless LAN), Wi-Fi (Wireless-Fidelity), Wi-Fi (Wireless Fidelity) Direct, DLNA (Digital Living Network Alliance), WiBro (Wireless Broadband), WiMAX (World Interoperability for Microwave Access), HSDPA (High Speed Downlink Packet Access), HSUPA (High Speed Uplink Packet Access), LTE (Long Term Evolution), LTE-A (Long Term Evolution-Advanced), and the like. The wireless Internet module 113 may transmit/receive data according to one or more of such wireless Internet technologies, and other Internet technologies as well.

Considering that wireless Internet access based on the WiBro, HSDPA, HSUPA, GSM, CDMA, WCDMA, LTE, LTE-A and the like is performed through a mobile communication network, the wireless Internet module 113, which performs the wireless Internet access through the mobile communication network, may be considered as the mobile communication module 112.

The short-range communication module 114 is configured to facilitate short-range communications. Suitable technologies for implementing such short-range communications include Bluetooth™, RFID (Radio Frequency Identification), IrDA (Infrared Data Association), UWB (Ultra Wideband), ZigBee, NFC (Near Field Communication), Wi-Fi (Wireless-Fidelity), Wi-Fi Direct, Wireless USB (Wireless Universal Serial Bus) and the like. In general, the short-range communication module 114 may support wireless communications between the mobile terminal 100 and a wireless communication system, communications between the mobile terminal 100 and another mobile terminal 100, or communications between the mobile terminal 100 and a network where another mobile terminal 100 (or an external server) is located, via wireless area networks. One example of the wireless area networks is a wireless personal area networks.

In some cases, another mobile terminal 100 (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may transmit at least part of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is a module for obtaining a (current) position of the mobile terminal. Examples of the location information module 115 includes a Global Position System (GPS) module and a Wi-Fi module. For example, when the mobile terminal uses the GPS module, the position of the mobile terminal may be acquired using a signal sent from a GPS satellite. As another example, when the mobile terminal uses the Wi-Fi module, the position of the mobile terminal can be acquired based on information with respect to a wireless access point (AP) which transmits or receives a radio signal to or from the Wi-Fi module. If desired, the location information module 115 may alternatively or additionally function with any of the other modules of the wireless communication unit 110 to obtain data related to the position of the mobile terminal. In other words, the location information module 115 is used to obtain the (current) position of the mobile terminal but it is not limited to a module for directly calculating or obtaining the position of the mobile terminal.

Next, the input unit 152 will be described in detail. The input unit 120 is configured to receive information inputted by a user such as image information (or signal) or audio information (or signal). To receive the image information, the mobile terminal 100 may have one or a plurality of cameras 121. Such cameras 121 may process image frames of still pictures or video obtained by image sensors in a video or image capture mode. The processed image frames can be displayed on the display unit 151. In some cases, the cameras 121 may be arranged in a matrix configuration to permit a plurality of images having various angles or focal points to be input to the mobile terminal 100. In addition, the cameras 121 may be located in a stereoscopic arrangement to acquire left and right images for implementing a stereoscopic image.

The microphone 122 is configured to covert an external acoustic signal into electric audio data. The converted audio data can be variously utilized according to a function (or an application program) being executed in the mobile terminal 100. If necessary, the microphone 122 may include various noise removing algorithms to remove undesired noise generated in the course of receiving the external acoustic signal.

The user input unit 123 is a component for receiving information from a user. Once the information is inputted by the user, the controller 180 may control the mobile terminal 100 to perform an operation corresponding to the inputted information. The user input unit 123 may include a mechanical input means (or mechanical key) (e.g., a button, a dome switch, a jog wheel, a jog switch, and the like located on a front and/or rear surface or a side surface of the mobile terminal 100). As one example, a touch-sensitive input means may be a virtual key, a soft key, or a visual key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense at least one of internal information of the mobile terminal, surrounding environment information of the mobile terminal, and user information and generate a sensing signal in response to the sensed information. The controller 180 may control operation of the mobile terminal 100 or execute data processing, a function or an operation associated with an application program installed in the mobile terminal based on the sensing signal provided by the sensing unit 140. The sensing unit 140 may be implemented using any of a variety of sensors, some of which will now be described in more detail.

The proximity sensor 141 means a sensor capable of sensing a presence of an object approaching a surface, or an object located near a surface, by using an electromagnetic field, infrared rays, or the like without a mechanical contact. The proximity sensor 141 may be arranged at an inner region of the mobile terminal covered by the touch screen or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared ray proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

For convenience of description, the term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, proximity touch distance, proximity touch direction, proximity touch speed, proximity touch time, proximity touch position, proximity touch moving status, and the like). In general, the controller 180 may process data corresponding to proximity touches and proximity touch patterns sensed by the proximity sensor 141 and output visual information on the touch screen. In addition, the controller 180 can control the mobile terminal 100 to execute different operations or process different data according to whether a touch input at the same position on the touch screen is either the proximity touch or the contact touch.

A touch sensor can sense a touch (or touch input) applied to the touch screen (or display unit 151) using any of a variety of touch methods. Examples of such touch methods include a resistive type, a capacitive type, an infrared type, and a magnetic field type, among others.

As one example, the touch sensor may be configured to convert pressure applied to a specific portion of the display unit 151 or a change in capacitance occurring at a specific portion of the display unit 151 into an electric input signal. The touch sensor may also be configured to sense not only a touched position and a touched area, but also touch pressure and/or touch capacitance. A touch object means an object used to apply a touch input to the touch sensor. Examples of typical touch objects include a finger, a touch pen, a stylus pen, a pointer, and the like.

When a touch input is sensed by a touch sensor, a corresponding signal(s) may be transmitted to a touch controller. The touch controller may process the received signal (s) and then transmit corresponding data to the controller 180. Accordingly, the controller 180 may sense which region of the display unit 151 has been touched. Here, the touch controller may be provided separately from the controller 180 or correspond to the controller 180.

In some cases, the controller 180 may execute the same or different control according to a type of touch object that touches the touch screen (or a touch key provided in addition to the touch screen). Whether the controller 180 executes the same or different control according to the type of touch object may be determined based on a current operating state of the mobile terminal 100 or a currently executed application program.

The above-described touch sensor and proximity sensor may be implemented individually, or in combination, to sense various types of touches. Such touches include a short (or tap) touch, a long touch, a multi-touch, a drag touch, a flick touch, a pinch-in touch, a pinch-out touch, a swipe touch, a hovering touch, and the like.

The ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. Particularly, the position of the wave generation source may be calculated using the time difference from the time that the ultrasonic wave reaches the sensor based on the light as a reference signal.

In terms of configuration of the input unit 120, the camera 121 typically includes at least one a camera sensor (CCD, CMOS etc.), a photo sensor (or image sensors), and a laser sensor.

By implementing the camera 121 with a laser sensor, a touch of a physical object with respect to a 3D stereoscopic image can be detected. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Hereinafter, details of the user input unit 123 will be described. According to the present invention, the user input unit 123 may include a front input unit 231 and a rear input unit 232. In the following, a detailed structure of the user input unit 123 and an operation performed by the user input unit 123 will be explained.

Figure 2A:
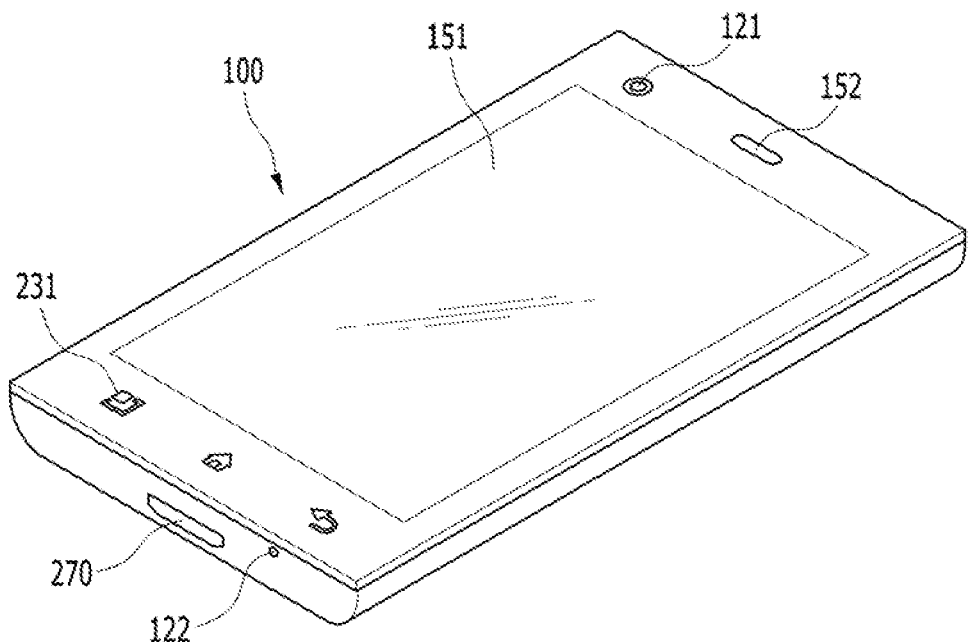
FIGS. 2a and 2b are diagrams illustrating an example of a mobile terminal according to an embodiment of the present invention.
Figure 2B:
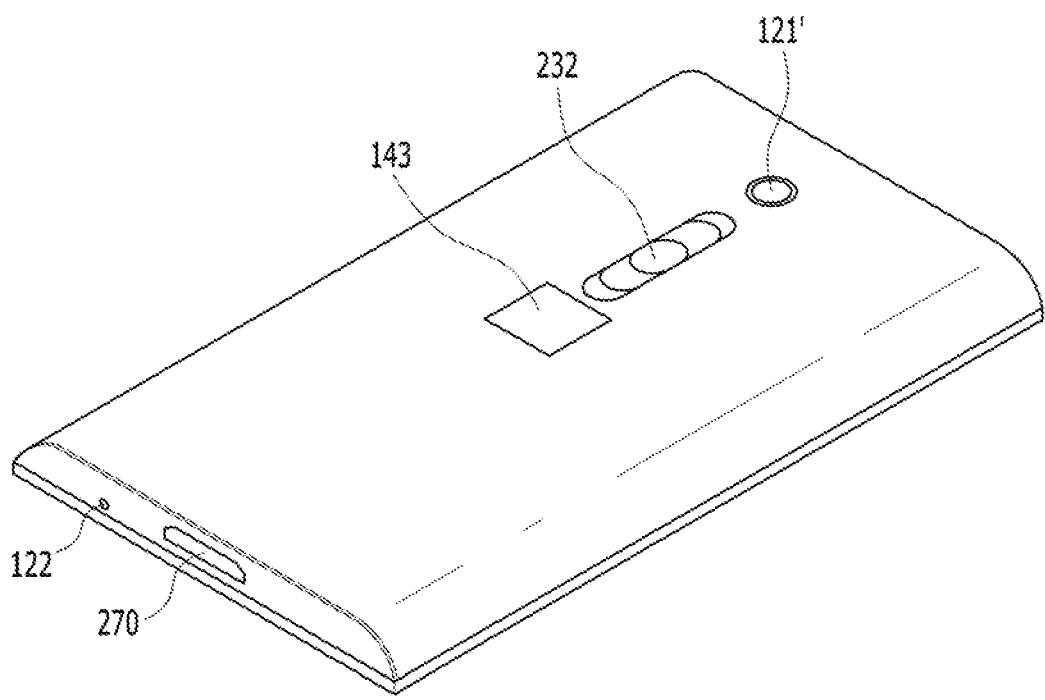

FIG. 2a is a front perspective view illustrating an example of a mobile terminal according to the present invention and FIG. 2b is a rear perspective view of the mobile terminal illustrated in FIG. 2a.

The disclosed mobile terminal 200 has a bar type terminal body. However, the present invention is not limited thereto and may be applicable to various structures such as a slide type mobile terminal, a folder type mobile terminal, a swing type mobile terminal, a swivel type mobile terminal, etc., in which two or more bodies are combined to be relatively movable.

The body includes a case (or casing, housing, cover, etc.) constituting the external appearance. In this embodiment, the case may include a front case 201 and a rear case 202. Various electronic components are installed in the space between the front case 201 and the rear case 202. One or more intermediate cases may be additionally disposed between the front case 201 and the rear case 202.

The cases may be formed by injection-molding a synthetic resin or may be made of a metallic material such as stainless steel (STS), titanium (Ti), or the like.

The display unit 151, the audio output unit 152, the camera module 121, etc. may be disposed mainly on the front case 201 of the terminal body. An interface 270 may be disposed on sides of the front case 201 and the rear case 202.

The display unit 151 occupies the most of a main surface of the front case 201. That is, the display unit 151 is disposed on the front side of the terminal and configured to display visual information. The audio output unit 152 and the camera module 121 are disposed at a region adjacent to one end portion among both end portions of the display unit 151, and the front input unit 231 and the microphone 122 are disposed at a region adjacent to another end portion.

The front input unit 231 is an example of the user input unit 130 and may include a plurality of manipulation units. The manipulation units may be generally referred to as a manipulating portion and various methods and techniques may be employed for the manipulation portion as long as they can be operated by the user in a tactile manner In the present invention, the front input unit 231 is configured as a touch key. However, the present invention is not limited thereto and a push key may be added to the front input unit 231.

Also, the display unit 151 may form a touch screen together with a touch sensor and in this case, the touch screen may be a user input unit. Through this, a configuration without a front input unit on the front side of the terminal may also be used. In this case, the mobile terminal may be configured such that an input manipulation with respect to the terminal body may be performed only through the display unit 151 and the rear input unit 232 as described hereinafter.

Referring to FIG. 2b, a camera module 121' may additionally be disposed on the rear case 202 of the terminal body. The camera module 121' may have an image capture direction which is substantially opposite to that of the camera module 121 and have a different number of pixels than the camera module 121.

For example, the camera module 121 may have a smaller number of pixels to capture an image of the user's face and transmit such image to a counterpart and the camera module 121' may have a larger number of pixels to capture an image of a general object and not immediately transmit it in most cases. The camera modules 121 and 121' may be installed on the terminal body such that they can be rotatable or popped up.

A flash and a mirror may be additionally disposed to be adjacent to the camera module 121'. When an image of a subject is captured with the camera module 121', the flash illuminates the subject. The mirror allows the user to see himself when the user desires to capture his own image (i.e., self-image capturing) by using the camera 121 module 121'.

An audio output unit (not shown) may be additionally disposed on the rear side of the terminal body. The audio output unit of the rear side may implement a stereoscopic function along with the audio output unit 151 of the front side and may be used for implementing a speaker phone mode during call communication.

The rear input unit 232 is disposed on the rear side of the terminal body. For instance, the rear input unit 232 may be positioned below the camera module 121'.

The rear input unit 232 may be manipulated to receive a command for controlling an operation of the mobile terminal 100 and input contents may be variously set. For example, the rear input unit 232 receive a command such as ON/OFF of power, starting, ending, scrolling, etc., a command such as controlling of the volume of a sound output from the audio output unit 152 or conversion into a touch recognition mode of the display unit 151.

The rear input unit 232 of the present invention is implemented to be available for push input. In detail, the rear input unit 232 may be configured as a mechanical or physical button, which is a relative concept with respect to a touch screen.

A biometric authentication sensor 143 is disposed adjacent to the rear input unit 232 at the rear side of the mobile terminal 100. For instance, the biometric authentication sensor 143 may be disposed adjacent to a bottom portion of the rear input unit 232. The biometric authentication sensor 143 senses a user's biometric signal. Here, the biometric signal may include information on at least one of a pattern of a user's finger blood vessel (i.e., finger vein), a change in blood flow in the user's finger blood vessel, and a change in color of a user's finger.

Figure 3:
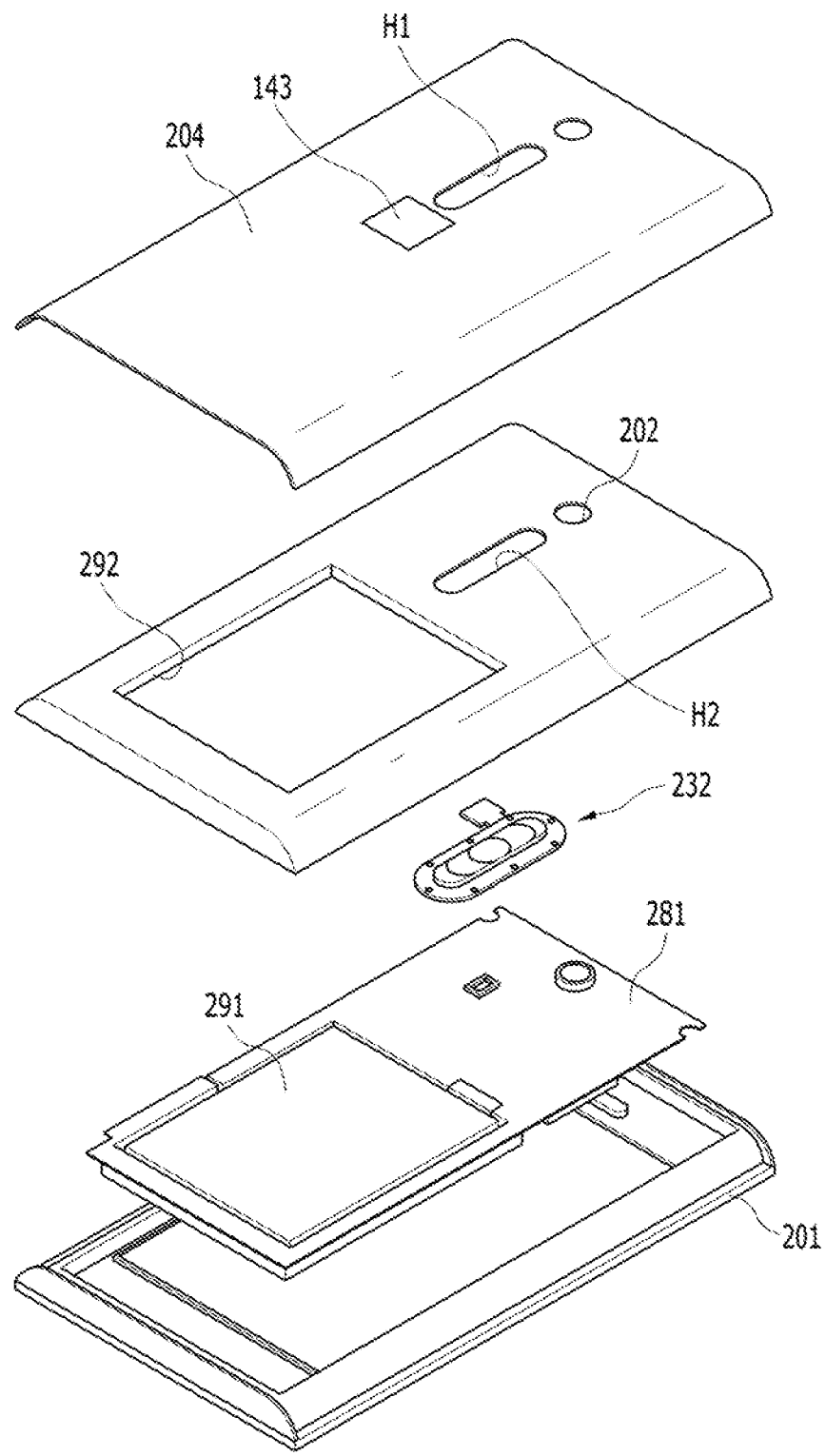
FIG. 3 is an exploded view of the mobile terminal shown in FIG. 2b.
Figure 4A:
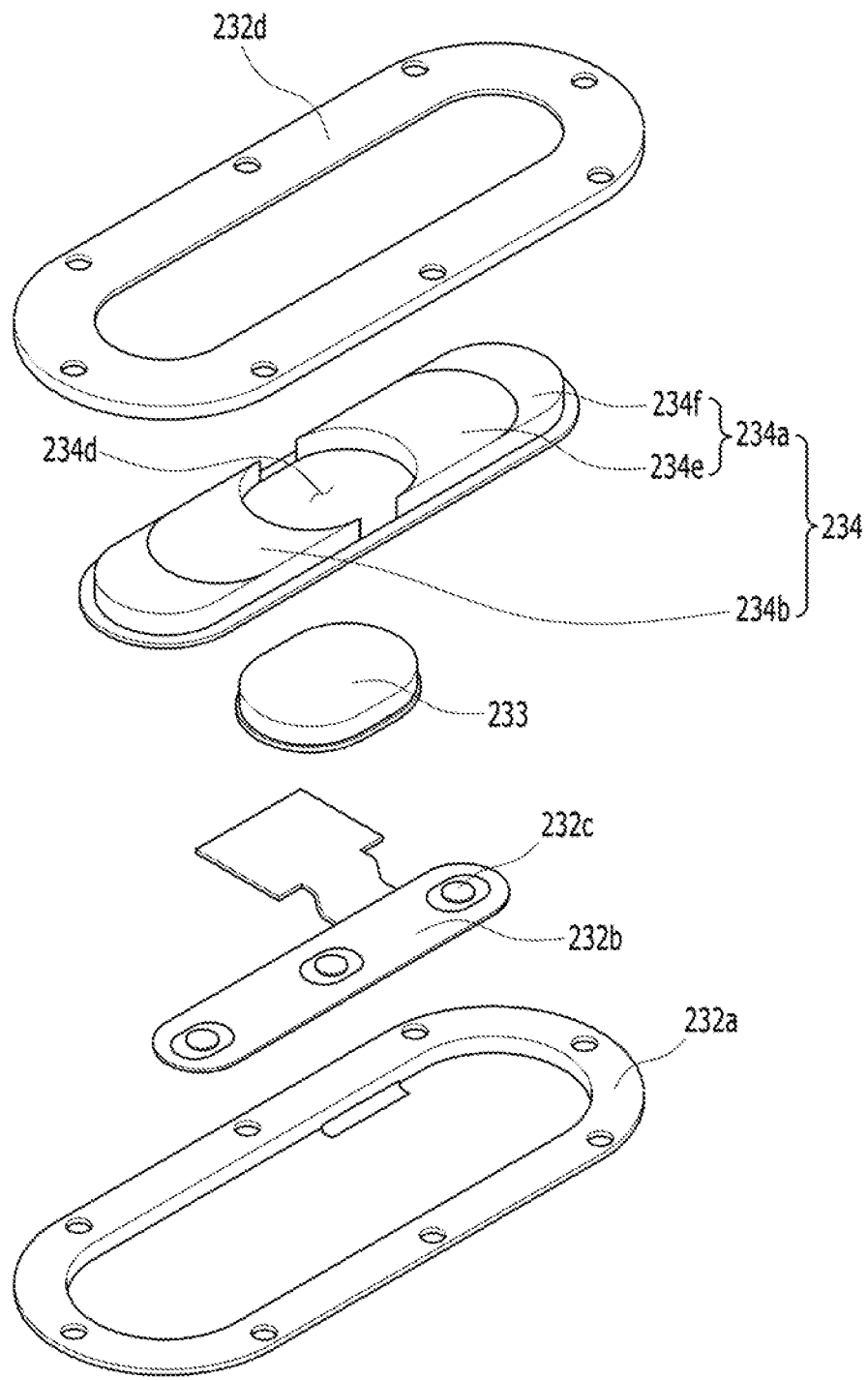

Hereinafter, a configuration of the rear input unit 232 will be described in detail. FIG. 3 is an exploded view of the mobile terminal shown in FIG. 2b and FIGS. 4a and 4b are a detailed exploded view and a cross-sectional view of the rear input unit shown in FIG. 3.

First of all, the rear input unit 232 and the surrounding components thereof are described with reference to the drawings. A printed circuit board (PCB) 281 is installed in the terminal body. For example, the PCB 281 may be installed in the front case 201 or the rear case 202 or may be installed in a separate structure 203. The separate structure 203 may form an intermediate case. Here, it is described that the front case 201 or the rear case 202 are separately configured, but the present invention is not limited thereto and the cases 201, 202, and 203 may be integrally formed.

The PCB 281 is configured as an example of the controller 180 (see FIG. 1) for operating various functions of the mobile terminal. The PCB 281 may be provided in plurality and the plurality of PCBs may be combined to perform a function of the controller 180. In order to perform such a function, various electronic elements are installed on the PCB 281.

In addition, the PCB 281 is electrically connected to an antenna (not shown in the drawings) and configured to process a radio signal corresponding to an electromagnetic wave transmitted and received by the antenna. The antenna is disposed between the separate structure 203 and the PCB 281 to transmit and receive a radio signal mainly through the rear case 202.

Referring to the drawings, the PCB 281 may be electrically connected to the camera module 121'. A battery loading portion 292 for loading a battery 291 is formed on the rear case 202 and a battery cover 204 for covering the battery loading portion 292 is installed on the case.

In addition, a through-hole (H2 and H1) is formed in each of the rear case 202 and the battery cover 204, and the camera module 121' is disposed to view the outside through the through-holes. The camera module 121' is configured to capture an external image through the rear side of the terminal.

Referring back to the rear input unit 232, in order to prevent formation of a recess on a side surface of the terminal body in the length direction due to the user input unit, the rear input unit 232 overlaps the display unit 151 in the thickness direction of the terminal body and is exposed to the rear side of the terminal body, rather than to the side surface thereof. Hereinafter, a detailed structure of the rear input part 232 and a side surface structure of the terminal will be described.

The rear input unit 232 may be disposed between the camera module 121' and the battery. The rear input unit 232 may be positioned to overlap the display unit 151 of the front side of the terminal. Through this structure, a user may sense that the input device is disposed on the back side of the display unit 151. However, the present invention is not limited thereto and the position of the rear input unit 232 may be modified. As illustrated, the battery cover 204 has the through-hole H1 corresponding to the rear input unit 232. In addition, the trough-hole H2 corresponding to the through-hole H1 may be formed on the rear case 202.

As shown in FIG. 4a, a support member 232a is installed in the rear case 202 to support the rear input unit 232. More specifically, the support member 232a is disposed in a position corresponding to the through-hole H2. At least a part of the bottom portion of the support member 232a is opened and the inside and outside of the support member 232a are electrically connected with each other through wiring of a PCB 232b based on the opening. The PCB 232b may be configured as a flexible PCB and be disposed at the center of the support member 232a. In addition, switches 232c may be disposed on the PCB 232b. The switches may be a dome switch, a piezoelectric switch, and the like.

Moreover, the rear input unit 232 includes a plurality of buttons corresponding to the switches, for example, a first button part 233 and a second button part 234. The first button part 233 is exposed to the outside form the rear side of the terminal and is configured to receive a push input of a first function. The first function may be a function related to ON/OFF of power or activation of the display unit 151. Thus, the first button part 233 may be a power key of the terminal.

The second button part 234 includes keys 234a and 234b disposed on both sides of the first button part 233 and is configured to receive a push input of a second function different from the first function. The second function may be a function related to adjustment of a volume of sound outputted from the main body of the terminal.

Further, a guide member 232d for guiding movement of the second button part 234 is included as a support member. A hole is formed at the center of the guide member 232d such that the second button part 234 is located at the hole and the edges of the second button part 234 are combined with the support member 232a. In addition, as shown in FIG. 4b, a hang wing 234c may be formed along an outer circumferential surface of the second button part 234 such that the edges of the second button part 234 are internally located.

The first button part 233 is formed to penetrate through the second button part 234 between the keys 234a and 234d. That is, a through-hole 234d is formed in the second button part 234. As illustrated, the keys 234a and 234b are formed as protruded surfaces by being exposed to the outside and the opposite side of the protruded surfaces are formed flatly. Therefore, a user may distinguish between the keys in a tactile manner.

More specifically, in order to form a height difference between the keys 234a and 234b and the first button part 233, the keys 234a and 234b have an inclined surface 234e inclined towards the through-hole 234d. The inclined surface 234e is adjacent to the first button part 233 among the protruded surfaces and it may be formed as a curved surface. The first button part 233 is formed such that it protrudes outwardly, compared to an end portion of the inclined surface 234e. In addition, the keys 234a and 234b have a subordinate inclined surface 234f, which is inclined toward the direction opposite to that of the inclined surface 234e, at an area adjacent to the guide member. The first button part 233 and the second button part 234 may be formed of different materials. Through this structure and material, the user may easily distinguish between the first button part 233 and the second button part 232 through the structure and the material.

Although the present invention is described based on the case in which three buttons i.e., the key 233 located at the center of the rear input unit 232 and the keys 234a and 234b located at both ends of the rear input unit 232, are configured, the invention is not limited thereto. For instance, the rear input unit 232 may have a single button or five buttons i.e., the key 233 located at the center of the rear input unit 232 and four other keys located at cardinal points with respect to the key 233. Further, the following description is made on the assumption that the rear input unit 232 has the three buttons but functions defined in terms of any of the three buttons can be applied to the single button or five buttons.

Figure 5:
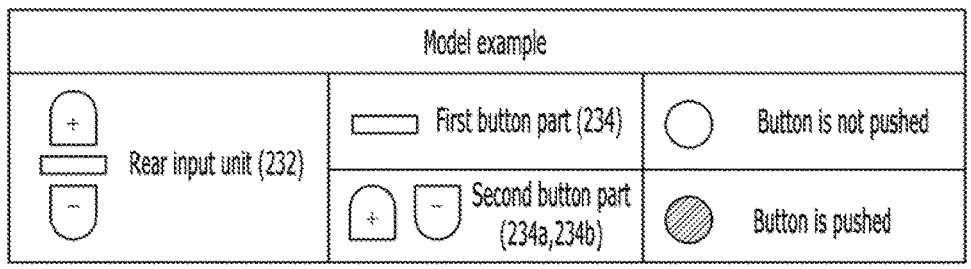
FIG. 5 is a diagram illustrating input combinations for the rear input unit, functions indicated by the input combinations, and a mapping relationship between the input combinations and applications.

As shown in the example illustrated in FIG. 5, the mobile terminal 100 may store input combinations for the rear input unit 232 and a relationship (e.g., mapping table) between control commands of the mobile terminal 100 associated with the input combinations and related functions in the memory 170. In this case, if a user pushes a specific input combination through the rear input unit 232, the controller 180 may retrieve a control command indicated by the pushed input command from the mapping table and then execute the retrieved control command.

It is apparent that various combinations can be used as well as the input combinations illustrated in FIG. 5. In addition, the mapping relationship between the input combinations and the applications (or functions) may be changed by the user.

Referring to FIG. 5, if the controller senses that a button is initially pushed (for example, when the first button part 234 is initially pushed), the controller 180 may release a power saving mode of the mobile terminal 100. Thereafter the controller 180 may control a pre-designated application or function to be executed according to a combination of pushed buttons. That is, in the items 2 to 4 illustrated in FIG. 5, the initial push of the first button part 234 may wake up the mobile terminal 100 from the power saving mode and other push inputs may call the predetermined function or application.

Figure 6:
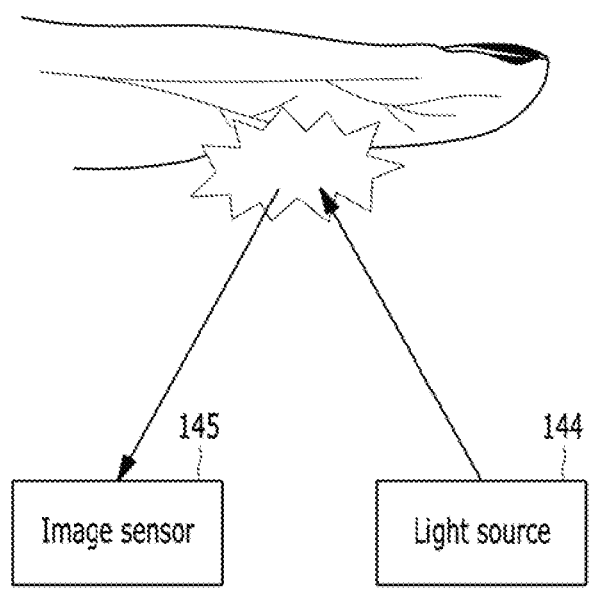
FIG. 6 is a diagram an example of a configuration of a biometric authentication sensor according to the present invention and an operation thereof.

FIG. 6 is a diagram for explaining a configuration of the biometric authentication sensor 143 according to the present invention and an operation thereof.

As shown in FIG. 6, the biometric authentication sensor 143 of the present invention may include a light source 144 and an image sensor 145. The light source 144 includes a device capable of emitting light to a user's finger. For example, the light source 144 may be configured with an LED capable of emitting infrared light. The image sensor 145 senses a user's biometric signal based on reflected light reflected from the user's finger. To this end, the image sensor 145 photographs the finger. That is, the user's biometric signal is included in an image or video captured by the image sensor 145 and the controller 180 extracts the biometric signal from the captured image or video. For instance, the controller 180 detects at least one of a pattern of a user's finger vessel (i.e., finger vein), a change in blood flow in the user's finger blood vessel, and a change in color of the user's finger. In particular, the controller 180 uses a video captured during a predetermined time to detect the change in the finger blood flow and the change in the finger color.

Figure 7:
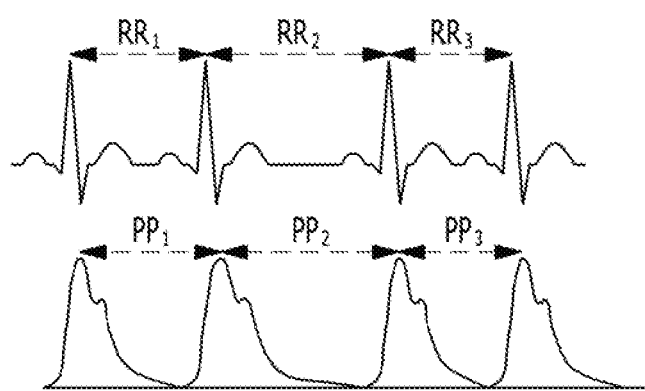
FIG. 7 is a diagram illustrating examples of signals detected and outputted by the biometric authentication sensor according to the present invention.

FIG. 7 illustrates a change in blood flow detected from a captured video. As shown in FIG. 7, the controller 180 measures the change in the blood flow in the vein from the captured video and then detects a photoplethysmogram (PPG) for estimating a cardiac activity state. Using the PPG, the controller 180 may determine whether the finger belongs to a living human being or whether the biometric signal is forged/falsified.

Figure 8:
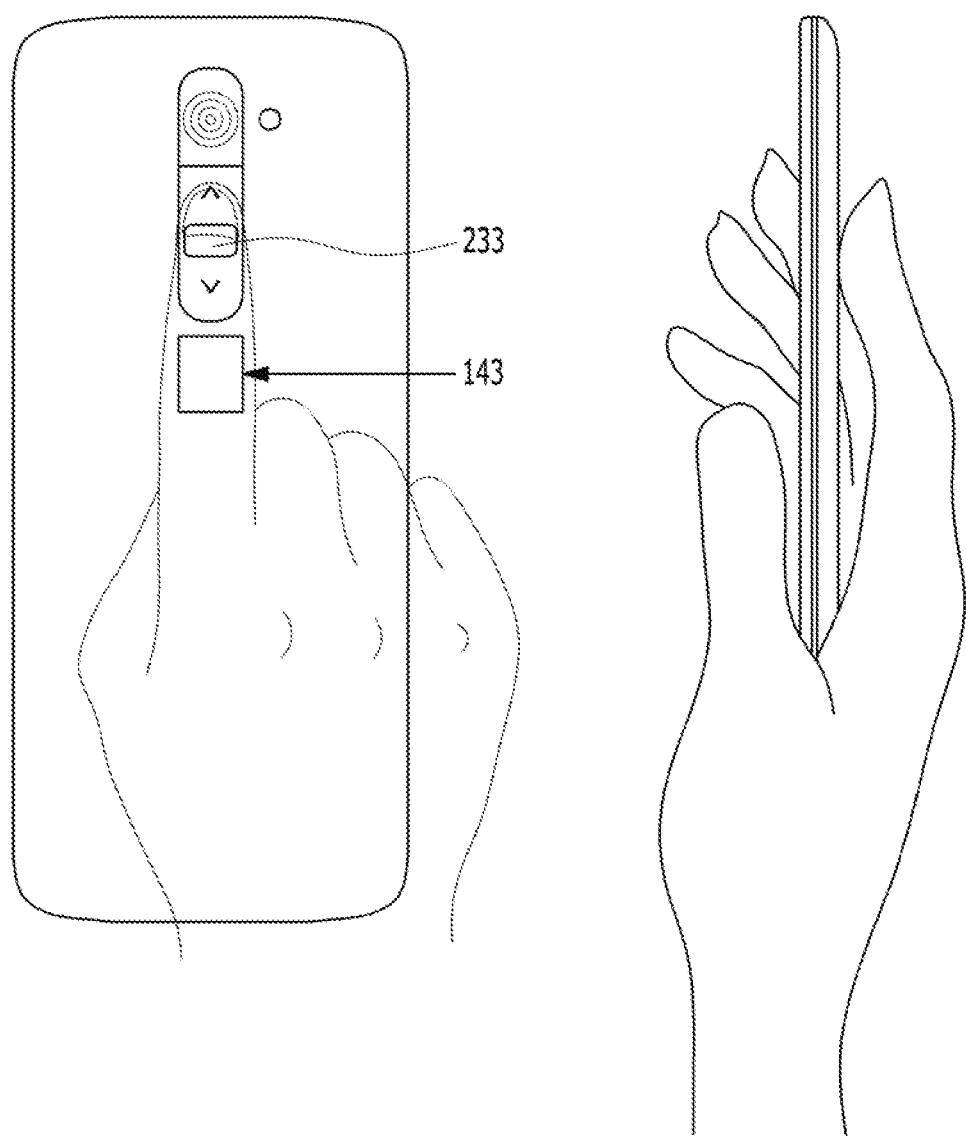
FIG. 8 is a diagram for explaining an example of an operation of the mobile terminal according to the present invention.

FIG. 8 is a diagram for explaining an example of an operation implemented by the present invention.

First of all, when a user input is received through a specific combination of the buttons of the rear input unit 232, the controller 180 controls the biometric authentication sensor 143 to sense a user's biometric signal in response to the user input.

Thereafter, the controller 180 authenticates the user by using the sensed biometric signal and previously stored biometric information. In the case, several methods can be used for user authentication.

According to a first method for the user authentication, the controller 180 may authenticate the user by using the sensed biometric signal and biometric information pre-stored in the memory 170. To this end, the controller 180 compares the user's finger blood vessel pattern indicated by the sensed biometric signal with a blood vessel pattern indicated by the pre-stored biometric information and then authenticates the user in accordance with the comparison result. For instance, when the two blood vessel patterns match with each other, the controller 180 recognizes the user as a registered user. Otherwise, the controller 180 recognizes the user as a non-registered user.

According to a second method for the user authentication, the controller 180 transmits the sensed biometric signal to a server and the server compares the sensed biometric signal with pre-stored biometric information. Thereafter, the server can authenticate the user. To this end, the server compares the user's finger blood vessel pattern indicated by the sensed biometric signal with a blood vessel pattern indicated by the pre-stored biometric information and then authenticates the user in accordance with the comparison result. For instance, when the two blood vessel patterns match with each other, the server recognizes the user as the registered user. Otherwise, the server recognizes the user as the non-registered user.

Further, the controller 180 can determine whether the sensed biometric signal is forged or copied. That is, the controller 180 may use at least one of the change in the blood flow in the user's finger blood vessel and the change in the color of the user's finger in order to determine whether the biometric signal is forged/copied. For instance, if the at least one of the change in the blood flow in the user's finger blood vessel and the change in the color of the user's finger is changed according to a certain pattern, the controller 180 may determine that the biometric signal is not forged or copied.

Figure 9:
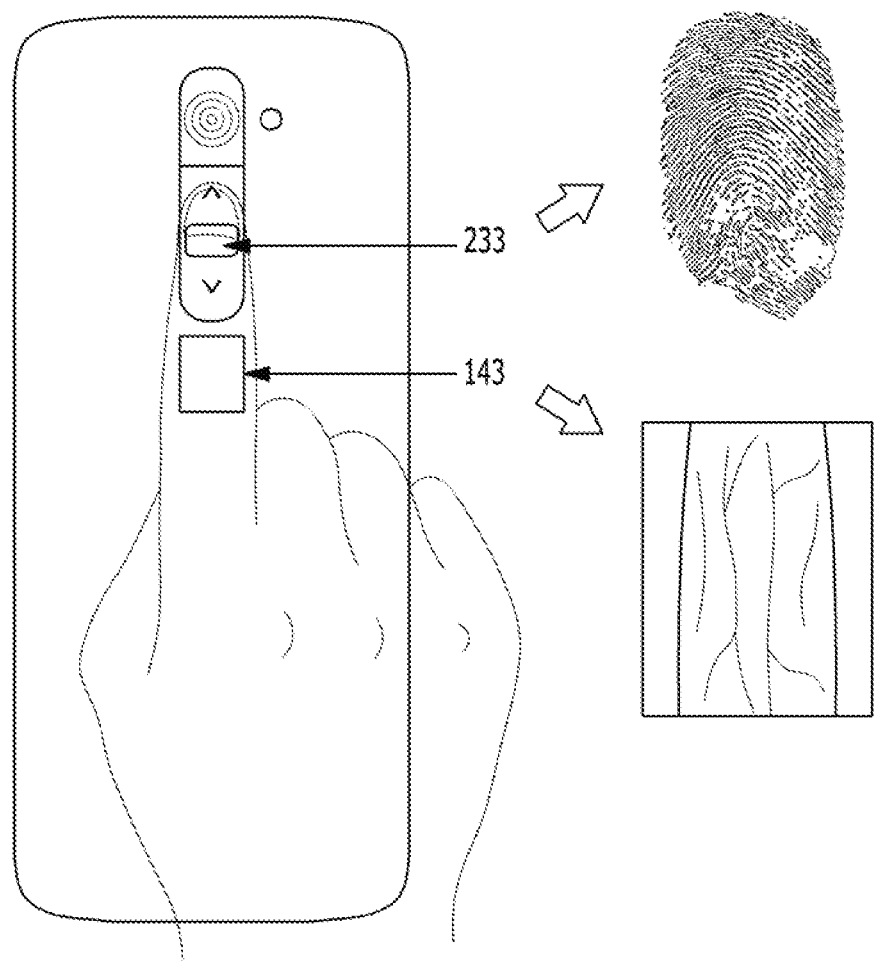
FIG. 9 is a diagram for explaining another example of an operation of the mobile terminal according to the present invention.

FIG. 9 is a diagram for explaining another example of an operation implemented by to the present invention.

First of all, when a user input is received through a specific combination of the buttons of the rear input unit 232, the controller 180 controls the rear input unit 232 to sense a user's fingerprint and the biometric authentication sensor 143 to sense a user's biometric signal in response to the user input. In the case, the sensing of the user's finger print and the user's biometric signal may be performed according to a predetermined order or a random order. In the case of the predetermined order, the controller 180 first controls the rear input unit 232 to sense the user's fingerprint and then controls the biometric authentication sensor 143 to sense the user's biometric signal. In the case of the random order, the controller 180 may control the rear input unit 232 and the biometric authentication sensor 143 to sense any of the fingerprints and the biometric signal which can be first sensed. In addition, in this case, the rear input unit 232 further includes a fingerprint sensor for sensing a user's fingerprint and the fingerprint sensor may be integrated with the first button part 233.

Thereafter, the controller 180 authenticates the user by using the sensed fingerprint and biometric signal. In the case, several methods can be used for user authentication.

According to a first method for the user authentication, the controller 180 may authenticate the user by using the sensed fingerprint and biometric signal, and biometric information pre-stored in the memory 170. To this end, the controller 180 compares the sensed fingerprint with fingerprint information contained in the pre-stored biometric information and compares the user's finger blood vessel pattern indicated by the sensed biometric signal with a blood vessel pattern indicated by the pre-stored biometric information and then authenticates the user in accordance with the comparison results. For instance, when the sensed fingerprint matches with the pre-stored fingerprint information and the two blood vessel patterns match with each other, the controller 180 recognizes the user as a registered user. When the sensed fingerprint does not match with the pre-stored fingerprint information or the two blood vessel patterns do not match with each other, the controller 180 recognizes the user as a non-registered user.

According to a second method for the user authentication, the controller 180 transmits the sensed fingerprint and biometric signal to a server and the server compares the sensed fingerprint and biometric signal with pre-stored biometric information. Thereafter, the server can authenticate the user. To this end, the server compares the sensed fingerprint with fingerprint information contained in the pre-stored biometric information and compares the user's finger blood vessel pattern indicated by the sensed biometric signal with a blood vessel pattern indicated by the pre-stored biometric information and then authenticates the user in accordance with the comparison results. For instance, when the sensed fingerprint matches with the pre-stored fingerprint information and the two blood vessel patterns match with each other, the controller 180 recognizes the user as a registered user. When the sensed fingerprint does not match with the pre-stored fingerprint information or the two blood vessel patterns do not match with each other, the controller 180 recognizes the user as a non-registered user.

Further, the controller 180 can determine whether the sensed biometric signal is forged or copied. That is, the controller 180 may use at least one of the change in the blood flow in the user's finger blood vessel and the change in the color of the user's finger in order to determine whether the biometric signal is forged/copied. For instance, if the at least one of the change in the blood flow in the user's finger blood vessel and the change in the color of the user's finger is changed according to a certain pattern, the controller 180 may determine that the biometric signal is not forged or copied.

As another example of the operation implemented by the present invention, the mobile terminal 100 can be utilized as an IR scanner by using the biometric authentication sensor 143. That is, when the light source 144 emits infrared light, the image sensor 145 captures images using reflected light. Thereafter, the controller 180 may create a scanned image by combining the captured images.

Moreover, the mobile terminal 100 can be utilized as an interface (e.g., mouse) of a device such as a personal computer, laptop or the like by using the biometric authentication sensor 143. In this case, the light source 144 emits infrared light and the image sensor 145 senses a change in reflected light. In addition, the controller 180 may determine moving direction and distance of the mobile terminal 100 on the basis of the change in the light sensed by the image sensor 145.

The mobile terminal 100 according to the present invention can improve accuracy using user's biometric signal fingerprint and thus the mobile terminal 100 can be utilized in the financial payment where security is required. Moreover, the mobile terminal 100 can identify a finger of a living human being by extracting a user's cardiac signal, thereby preventing the biometric signal from being forged or copied.

According to an embodiment of the present invention, the above-described method (operation flowchart) can be implemented in a program recorded medium as processor-readable codes. The processor-readable media include ROM, RAM, CD-ROM, magnetic tapes, floppy disks, optical data storage devices, and the like for example and also include carrier-wave type implementations (e.g., transmission via Internet).

The aforementioned mobile terminal 100 is not limited to the configuration and method with respect to the above-described embodiments, and some or all of the embodiments may also be selectively combined so that various variations may be implemented.

What is claimed is:

1. A mobile terminal, comprising:
    a rear input unit including a plurality of buttons exposed at a rear side of the mobile terminal, the rear input unit comprising a fingerprint sensor for detecting a fingerprint of a user;
    a memory for storing relationships between combinations of the plurality of buttons for determining a predetermined order and control commands of the mobile terminal and biometric information;
    a sensor unit for sensing a biometric signal of the user, wherein the sensor unit is adjacent to a bottom portion of the rear input unit such that the sensor unit senses the biometric signal when the user's finger is on the rear input unit, the sensor unit comprising:
        a light source for emitting light to the finger of the user; and
        an image sensor for sensing the biometric signal from light reflected from the finger; and
    a controller,
    wherein when a user input corresponding to a specific combination of the plurality of the buttons is received, the controller controls the rear input unit to sense the user's fingerprint and controls the sensor unit to sense the biometric signal of the user according to the predetermined order, wherein the predetermined order is determined by matching the specific combination of the plurality of buttons to the stored relationships between the combinations of the plurality of buttons, and
    wherein when the fingerprint and biometric signal of the user are sensed, the controller authenticates the user by using the sensed fingerprint and biometric signal and the stored biometric information.

2. The mobile terminal of claim 1, wherein the biometric signal indicates a pattern of the user's finger vein.

3. The mobile terminal of claim 1, wherein the biometric signal indicates a change in blood flow in the user's finger vein.

4. The mobile terminal of claim 1, wherein the biometric signal indicates a change in a color of the user's finger.

5. The mobile terminal of claim 1, wherein:
    the controller compares a pattern of the user's finger vein indicated by the sensed biometric signal with a vein pattern indicated by the stored biometric information and authenticates the user based on a result of the comparison, and
    the controller recognizes the user as a registered user when the pattern of the user's finger vein matches with the vein pattern indicated by the stored biometric information, the user recognized as a non-registered user when the pattern of the user's finger vein does not match with the vein pattern indicated by the stored biometric information.

6. The mobile terminal of claim 1, wherein the controller determines whether the biometric signal is forged or copied by using at least one of a change in blood flow in the user's finger vein and a change in color of the user's finger, which are indicated by the biometric signal.

7. The mobile terminal of claim 1, wherein the rear input unit further comprises:
    a first button part; and
    a second button part with buttons disposed on both top and bottom portions of the first button part.

8. A method of controlling a mobile terminal with a rear input unit, which includes a plurality of buttons disposed at a rear side of the mobile terminal, the method comprising:
    receiving a user input corresponding to a specific combination of the plurality of buttons;
    in response to the user input, sensing a fingerprint of a user by a fingerprint sensor of the rear input unit and sensing a biometric signal of the user by a sensor unit according to a predetermined order, wherein the predetermined order is determined by matching the specific combination of the plurality of buttons to stored relationships between combinations of the plurality of buttons, the combinations of the plurality of buttons being stored for determining the predetermined order, wherein the sensor unit is adjacent to a bottom portion of the rear input unit such that the sensor unit senses the biometric signal when the user's finger is on the rear input unit, the rear input unit comprising:
        a light source for emitting light to the finger of the user; and
        an image sensor for sensing the biometric signal from light reflected from the finger; and
    authenticating the user by using the sensed fingerprint and biometric signal and pre-stored biometric information.

9. The method of claim 8, wherein the authenticating comprises:
    comparing a pattern of the user's finger vein indicated by the sensed biometric signal with a vein pattern indicated by the pre-stored biometric information; and
    authenticating the user based on a result of the comparison, and wherein the user is recognized as a registered user when the pattern of the user's finger vein matches with the vein pattern indicated by the pre-stored biometric information, and the user is recognized as a non-registered user when the pattern of the user's finger vein does not match with the vein pattern indicated by the stored biometric information.

10. The method of claim 8, further comprising:

determining whether the biometric signal is forged or copied by using at least one of a change in blood flow in the user's finger vein and a change in a color of the user's finger, which are indicated by the biometric signal.

\* \* \* \* \*